United States Patent [19]

Tokue et al.

[11] Patent Number: 5,776,438
[45] Date of Patent: Jul. 7, 1998

[54] EXTERNAL PREPARATION

[75] Inventors: Wataru Tokue; Kenzo Ito, both of Yokohama; Naoki Tominaga, Tokyo, all of Japan

[73] Assignee: Shiseido Co., Ltd., Tokyo, Japan

[21] Appl. No.: 645,681

[22] Filed: May 14, 1996

Related U.S. Application Data

[63] Continuation-in-part of Ser. No. 371,484, Jan. 11, 1995, abandoned, which is a continuation of Ser. No. 854,624, filed as PCT/JP90/01383, Oct. 18, 1990.

[51] Int. Cl.$^6$ .............................. A61K 7/42; A61K 31/66
[52] U.S. Cl. ........................ 424/59; 424/70.9; 424/401; 514/148; 514/454
[58] Field of Search .................. 424/401, 59, 70.9; 574/454, 148

[56] References Cited

U.S. PATENT DOCUMENTS

| | | | |
|---|---|---|---|
| 4,564,686 | 1/1986 | Ogata | 549/220 |
| 5,053,222 | 10/1991 | Takasu et al. | 424/7 |

*Primary Examiner*—Karen A. Dean
*Attorney, Agent, or Firm*—Townsend&Banta

[57] ABSTRACT

An external preparation containing DL-α-tocopherol 2-L-ascorbic phosphoric diester and/or a salt thereof, and at least one ultraviolet absorbing agent. The cross-linking of collagen is suppressed and an excellent cutaneous aging resisting effect is obtained.

11 Claims, No Drawings

EXTERNAL PREPARATION

Cross Reference to a Related Applications

This is a Continuation-In-Part patent application of application Ser. No. 08/371,484 filed Jan. 11, 1995, now abandoned, which is a file wrapper continuation application of application Ser. No. 07/854,624 filed Jun. 26, 1992 which claims priority of PCT application No. PCT/JP90/01383 filed Oct. 18, 1990.

FIELD OF THE INVENTION

The present invention relates to an external preparation and more particularly, to an external preparation which is applied to the skin to resist cutaneous aging.

BACKGROUND ART

The epidermis of the skin becomes thin with aging, and suffers from symptoms such as the reduction in the production of keratin.

One of the important factors affecting cutaneous aging is age in a broad view, but more direct causes are dryness, oxidization by active oxygen, damage by ultraviolet rays (especially UV-A ultravioletrays which reaches carium) and the like.

Various methods are conventionally taken in order to resist cutaneous aging. For example, external preparations applied to the skin containing a blend of various humectants for resisting cutaneous aging due to dryness, those containing an antioxidant such as vitamin E for resisting cutaneous aging due to oxidization, and those containing an absorbing agent for resisting cutaneous aging due to ultraviolet rays are conventionally used.

Such conventional cutaneous aging resisting means are no better than a symptomatic treatment, and cannot produce a sufficient cutaneous aging resisting effect.

SUMMARY OF THE INVENTION

Accordingly, it is an object of the present invention to eliminate the above described problems in the prior art and to provide an external preparation which is capable of resisting cutaneous aging more efficiently.

As a result of studies undertaken by the present inventors so as to achieve this aim, it has been found that an excellent cutaneous aging resisting effect is produced by combining a specific tocopherol derivative and an ultraviolet absorbing agent. The present invention has been achieved on the basis of this finding.

It is well known that the cross-linking of the collagen in the skin increases with aging (Cutaneous Aging, edited by Albert M. Kligman and Yoshio Takase, UNIVERSITY OF TOKYO PRESS, pp. 263 to 274, 1988 and Sugiyama T., Fujimoto D., Arai C., and Hasegawa M., Biomed. Res. 8: pp.349 to 351, 1987).

It is also known that collagen is cross-linked by ultraviolet rays (Fujimori E., FEBS Lett 235 (1 to 2) pp. 98 to 102, 1988).

Accordingly, the present inventors have aimed at production of an external preparation which resists cutaneous aging by suppressing cross-linking of the collagen in the skin.

In the first aspect of the present invention, an external preparation comprises: at least about 0.005 wt % of DL-α-tocopherol 2-L-ascorbic phosphoric diester and/or a salt thereof; and at least about 0.01 wt % of at least one ultraviolet absorbing agent.

In the second aspect of the present invention, the amount of said DL-α-tocopherol 2-L-ascorbic phosphoric diester and/or a salt thereof is 0.005 to 0.2 wt %.

In the third aspect of the present invention, the amount of said ultraviolet absorbing agent is 0.01 to 15.0 wt %.

In the fourth aspect of the present invention, an external preparation comprises;
from about 0.005 to 0.2 wt % of DL-α-tocopherol 2-L-ascorbic phosphoric diester and/or a salt thereof, and
from about 0.01 to 15.0 wt % of at least one ultrabiolet absorbing agent.

In the fifth aspect of the present invention, an external preparation comprises: DL-α-tocopherol 2-L-ascorbic phosphoric diester and/or a salt thereof, and at least one benzophenone ultraviolet absorbing agents.

In the sixth aspect of the present invention, an external preparation comprises: from about 0.005 to 0.2 wt % of DL-α-tocopherol 2-L-ascorbic phosphoric diester and/or a salt thereof and from about 0.01 to 15.0 wt % of at least one benzophenone ultraviolet absorbing agent.

In the seventh aspect of the present invention, the ultraviolet absorbing agent is 2- hydroxy-4-methoxybenzophenone or its salt.

In the eighth aspect of the present invention, a method of resisting cutaneous aging comprises applying to the skin said external preparation In the ninth aspect of the present invention, a preparation for resisting cutaneous aging when applied to the skin comprises DL-α-tocopherol 2-L-ascorbic phosphoric diester and/or salt thereof, and at least one benzophenone ultraviolet absorbing agents.

The structure of the present invention will be explained in detail hereinunder.

The amount of DL-α-tocopherol 2-L-ascorbic phosphoric diester (hereinunder referred to as "EPC") and/or a salt thereof in an external preparation for application to the skin according to the present invention is preferably 0.005 to 0.2 wt %.

An example of a preferred salt of EPC is alkali metal salts such as sodium and potassium, and alkali earth metal salts such as calcium and magnesium of EPC (hereinunder referred to as EPC-Na and the like).

If the amount of EPC is less than 0.005 wt %, it is sometimes impossible to obtain a sufficient cutaneous aging resisting effect. Addition of more than 0.2 wt % of EPC hardly increases the cutaneous aging resisting effect.

In the present invention, at least one ultraviolet absorbing agent is used in addition to EPC or a salt of EPC.

As the ultraviolet absorbing agent, ultraviolet absorbing agents which are permitted as ingredients of ordinary cosmetics are used as occasion demands. Examples thereof are:

cinamic acid ultraviolet absorbing agents such as 2-ethoxyethyl paramethoxy cinnamate, isopropyl paramethoxy cinnamate, diisopropyl cinnamate, ethylhexyl paramethoxy cinnamate, glyceryl diparamethoxy cinnamate mono-2-ethyl hexanoate and octyl methoxy cinnamate;

benzoylmethane ultraviolet absorbing agents such as butylmethoxybenzoylmethane and 4-tert-butyl-4'-methoxy-dibenzoylmethane;

bezophenone ultraviolet absorbing agents such as glyceryl-mono-2-ethylhexanoyl-di-paramethoxybenzophenone, 2-2'-dihydroxy-4-methoxybenzophenone, 2-2'-dihydroxy-4, 4'-dimethoxybenzophenone, 2-hydroxy-4-methoxybenzophenone and sodium 2-hydroxy-4-methoxybenzophenone-5-sulfonate;

benzoic acid ultraviolet absorbing agents such as methyl orthoaminobenzoate, 2-ethylhexyl-paradimethyl aminobenzoate and octyl paradimethyl aminobenzoate;

benzoate ultraviolet absorbing agents such as glyceryl paraaminobenzoate, amyl-para-dimethyl aminobenzoate and ethyl-4-bishydroxy propyl aminobenzoate; and other ultraviolet absorbing agents such as 2-ethylhexyl-2-cyano-3, 3'-diphenyl acrylate, digalloyl trioleate, 2-ethylhexyl salicylate, homomethyl salicylate, guaiazulene and urocanic acid.

The amount of ultraviolet absorbing agent added is different depending upon the type of ultraviolet absorbing agent, but it is generally 0.01 to 15.0 wt % of the total amount of external preparation.

If the amount of ultraviolet absorbing agent is less than 0.01 wt %, the synergistic effect thereof and EPC is sometimes insufficient. Addition of more than 15.0 wt % of ultraviolet absorbing agent hardly increases the cutaneous aging resisting effect.

In addition to the above-described essential ingredients, it is possible to add, if necessary, other ingredients which are used for ordinary cosmetics and drugs or quasi-drugs for application to skin. Those ingredients are, for example, vitamin A's such as vitamin A oil, retinol and retinol acetate; vitamin B2's such as riboflavin, riboflavin butyrate and flavin adenine dinulcleotide; vitamin B6's such as pyridoxine hydrochloride and pyridoxine dioctanoate; vitamin C's such as L-ascorbic acid, dipalmitate L-ascorbate, Na L-ascorbate-2-sulfate; pantothenic acids such as calcium pantothenate, D-pantothenyl alcohol, pantothenyl ethyl ether and acetylpantothenyl ethyl ether; vitamin D's such as ergocalciferol and cholecalciferol; nicotinic acids such as nicotinic acid, nicotinic acid amide, benzyl nicotinate; vitamin E's such as α-tocopherol, tocopherol acetate, DL-α-tocopherol nicotinate and DL-α-tocopherol succinate; other vitamins such as vitamin P and biotin; amino acids and derivatives thereof such as glycine, alanine, valine, leucine, isoleucine, serine, threonine, aspartic acid and salts thereof, glutamic acid and salts thereof lysine, arginine, cysteine, methionine, phenylalanine, tyrosine, histidine, tryptophane, proline, N-acyl acidic amino acid salts such as diethyl-N-palmitoyl L asparaginate and sodium N-coconut oil fatty acid-L-glutamate; acyl neutral amino acid salts such as coconut oil fatty acid-sarcosine triethanol amine and laurolylmethyl-β-alanine sodium; pyrrolidonecarboxylic acid and salts thereof, POE (40) hardened castor oil monopyrrogultamic monoisostearic diester and coconut oil fatty acid-L-ethyl arginate-DL-pyrrolidone-carboxylate; oil contents such as avocado oil, palm oil, peanut oil, beef tallow, rice bran oil, jojoba oil, evening primrose oil, carnauba wax, lanolin, liquid paraffin, squalane, isostearyl palmitate, isostearyl alcohol and glycerin tri-2-ethylhexanate; humectants such as glycerin, sorbitol, polyethylene glycol 1, 3-butylene glycol, collagen, hyaluronic acid, chondroitin sulfuric acid and sodium dextran sulfate; antioxidants such as sodium erisorbate and parahydroxyanisole; surfactants such as sodium stearyl sulfate, cetyl sulfate diethanol amine, cetyl trimethyl ammonium saccharin, polyethylene glycol isostearate, glyceryl arachate, diglycerin diisostearate and phospholipid; antiseptic agents such as ethyl para-hydroxybenzoate and butyl para-hydroxybenzoate; antiphlogistic agents such as glycyrrhizic acid, glycyrrhetic acid, salicylic acid derivative, hinokitiol, zinc oxide and allantoin; skin beautifiers such as extract of placenta, glutathione and extract of creeping saxifrage; various extracts such as extracts of phellodendron bark, goldthread, peony, Japanese green gentian, birch, sage, loquat, ginseng, aloe, mallow, iris, grape, coix seed, dishcloth gourd, lily, saffron, Cnidium officinare Makino, giner, Saint-John's wort, rosemary and garlic, vitalizers such as royal jelly, sensitizing dye, cholesterol derivatives and extract of calf's blood; blood circulation facilitators such as γ-oryzanol; anti-srborrhoeic agents such as sulfur and thianthol; thickening agents such as carboxyvinyl polymers, carboxymethyl cellulose and carboxylhydroxypropyl cellulose; perfumes; water; alcohols; coloring agents such as titanium yellow, carthamin and safflower red; and resin powder such as polyethylene and nylon powders.

The external preparation according to the present invention may take any given form. For example, it may be a soluble agent such as lotion, an emulsified agent such as milky lotion and cream, an ointment, a dispersant or an aerosol.

EMBODIMENTS

The present invention will be explained in detail with reference to preferred embodiments. The present invention, however, is not restricted to the embodiments.

Effect of ultraviolet rays in suppressing the cross-linking of collagen

A method of obtaining the ratio of cross-linking of collagen caused by ultraviolet rays will first be explained.

Collagen was extracted from human placenta with pepsin and salted out for purification (Nishihara T., and Miyata T., Collagen Symposium 3 pp. 66–93, 1962).

The purity of collagen measured 94% by electrophoresis (Hayashi T. and Nagai Y., J. Biochem. 86 (2), pp. 453 to 459, 1979). The extracted and purified collagen (final concentration; 1 mg/ml) was held in phosphate buffered saline of pH 7.4 at 37° C. to reconstruct collagen fiber, and thereafter the collagen fiber was irradiated with ultraviolet rays (TOSHIBA FL20S.BLB lamp, peak in the UV-A region: 365 nm) at an energy of 7.0 J/cm$^2$. Each of the sample shown in Tables 1 and 2 was allowed to coexist with collagen during irradiation.

Each sample was produced by mixing EPC-K and sodium 2-hydroxy-4-methoxybenzophenone-5-sulfonate as an ultraviolet absorbing agent with phosphoric buffer as a base.

The ratio of cross-linking of the collagen irradiated with ultraviolet rays was measured by electrophoresis and a densitometer (densitometer F-808 for fluorescence, produced by COSMO corporation).

The suppression ratio of the cross-linking of collagen was obtained from the following formula:

Suppression ratio =

$$100 - \frac{\text{cross-linking degree of collagen in sample}}{\text{cross-linking degree of collagen in reference}} \times 100$$

(Reference: phosphate buffered saline)

The results of experiments are shown in the following.

TABLE 1

| EPC | Ultraviolet absorbing agent | Suppression ratio |
|---|---|---|
| 0.5 | 5.0 | 80 |
| 0.3 | 5.0 | 77 |
| 0.2 | 5.0 | 82 |
| 0.1 | 5.0 | 85 |
| 0.05 | 5.0 | 84 |
| 0.01 | 5.0 | 79 |

TABLE 1-continued

| EPC | Ultraviolet absorbing agent | Suppression ratio |
|---|---|---|
| 0.005 | 5.0 | 72 |
| 0.001 | 5.0 | 61 |
| 0.0 | 5.0 | 56 |

As is obvious from Table 1, the preferred amount of EPC added is 0.05 to 0.2 wt %. When it was less than 0.005 wt %, an appropriate synergistic effect was not obtained. On the other hand, even by adding more than 0.2 wt % of EPC, the increase in the effect was not observed.

TABLE 2

| EPC | Ultraviolet absorbing agent | Suppression ratio |
|---|---|---|
| 0.1 | 20.0 | 80 |
| 0.1 | 15.0 | 85 |
| 0.1 | 10.0 | 79 |
| 0.1 | 5.0 | 85 |
| 0.1 | 1.0 | 83 |
| 0.1 | 0.5 | 72 |
| 0.1 | 0.1 | 81 |
| 0.1 | 0.05 | 77 |
| 0.1 | 0.01 | 71 |
| 0.1 | 0.005 | 61 |
| 0.1 | 0.0 | 57 |
| 0.0 | 0.0 | 56 |

As is obvious from Table 2, the preferred amount of ultraviolet absorbing agent added is 0.01 to 15.0 wt %. When it was less than 0.01 wt %, an appropriate synergistic effect was not obtained. On the other hand, even by adding more than 15.0 wt % of EPC, the increase in the effect was not observed.

As a result of these experiments, it was found that single use of either EPC or an ultraviolet absorbing agent cannot efficiently suppress the cross-linking of collagen.

A combination of another ascorbic acid or a derivative thereof did not produce the excellent effect in suppressing the cross-linking of collagen such as that described above.

TABLE 3

| L-ascorbic acid | Ultraviolet absorbing agent | Suppression ratio |
|---|---|---|
| 0.7 | 5.0 | 56 |
| 0.5 | 5.0 | 65 |
| 0.1 | 5.0 | 63 |

TABLE 4

| Tocopherol | Ultraviolet absorbing agent | Suppressing ratio |
|---|---|---|
| 0.7 | 5.0 | 40 |
| 0.5 | 5.0 | 55 |
| 0.1 | 5.0 | 58 |

TABLE 5

| Phosphate ascorbate | Ultraviolet absorbing agent | Suppression ratio |
|---|---|---|
| 0.7 | 5.0 | 38 |
| 0.5 | 5.0 | 47 |
| 0.1 | 5.0 | 53 |

As is obvious from Tables 3 to 5, single use of either ascorbic acid or tocopherol did not affect the suppression of the cross-linking of collagen in the above-described manner. Even use of an ascorbic acid derivative such as phosphate did not produce the synergistic effect, either.

In this way, it is observed that the action of suppressing the cross-linking of collagen is furthered by the idiosyncratic synergistic action of EPC and an ultraviolet absorbing agent.

The actual cutaneous aging resisting effect was examined by using hairless mice.

9-year-week hairless mice were divided into three groups, each consisting of three mice, and they were irradiated with ultraviolet rays from TOSHIBA 32BL lamp at a dosage of 14 J/cm2/day. 0.1 ml of a sample was applied to each mouse immediately before irradiation. 10 days after irradiation, 3 g of the skin was cut out and homogenized in 3% acetic acid. After incubating the homogenized skin for one night, it was subjected to centrifugal separation at a rate of 2000 rpm for 10 minutes. 5% trichloro acetic acid was added to the precipitate to effect acid hydrolysis at 90° C. for 30 minutes. After centrifugal separation at 2000 rpm for 10 minutes, the supernatant liquid was dialyzed and the hydroxyproline content in the collagen was measured by a method of Stagemann and Stalder (H. Stagemann and K stalder, Clinica Chemica Acta, 19, pp. 267 to 273, 1967) to calculate the amount of cross-linking collagen.

The composition of the sample liquid was as follows.

| Basic preparation | wt % |
|---|---|
| Citric acid | 0.02 |
| Sodium Citrate | 0.08 |
| Glycerin | 5.0 |
| Ethanol | 5.0 |
| Methyl para-hydroxybenzoate | 0.1 |
| Purified water | balance |

Group A (reference) . . . Basic preparation

Group B (Embodiment) . . . Basic preparation+EPC (0.2%)+sodium 2-hydroxy 4-methoxybenzophenone-5-sulfonate (1%)

Group C (Comparison) . . . Basic preparation+diisostearic acid L-ascorbin (1%)+sodium 2-hydroxy 4-methoxybenzophenone-5-sulfonate(1%)

The suppression ratio of the cross-linking of collagen was calculated in the above-described method The results are shown in Table 6.

TABLE 6

| | Suppression ratio |
|---|---|
| Group A | — |
| Group B | 87 |
| Group C | 50 |

Concrete examples of the composition of the external preparation of the present invention will now be shown. The amount of ingredient is shown by wt %. Each of external preparations produced the synergistic effect and the cutaneous aging resisting effect.

EXAMPLE 1

Lotion

| (1) EPC | 0.05 |
|---|---|
| (2) Sodium 2-hydroxy 4-methoxybenzophenone-5-sulfonate | 0.1 |
| (3) Tocopherol acetate | 0.01 |

-continued

| | |
|---|---|
| (4) Glycerin | 4.0 |
| (5) 1,3-butylene glycol | 4.0 |
| (6) Ethanol | 8.0 |
| (7) Polyoxyethylene (60) hardened castor oil | 0.5 |
| (8) Methyl para-hydroxybenzoate | 0.2 |
| (9) Citric acid | 0.05 |
| (10) Sodium citrate | 0.1 |
| (11) Perfume | 0.05 |
| (12) Purified water | balance |

<Process>

EPC, sodium 2-hydroxy-4-methoxybenzophenone-5-sulfonate, citric acid, sodium citrate, glycerin and 1,3-butylene glycol were dissolved in purified water. Separately from this, polyoxyethylene (60) hardened castor oil, tocopherol acetate, perfume and methyl para-hydroxybenzoate were dissolved in ethanol. The latter solution was added to the purified water solution for solubilization, and the resultant solution was filtered to obtain lotion.

<Result>

| Sample | Suppressing Ratio |
|---|---|
| Example 1 | 78 |
| Without UV absorbent (component (2)) | 47 |
| Without EPC (component (1)) | 39 |
| Without UV absorbent and EPC (components (1) and (2)) | 38 |

EXAMPLE 2

Cream

| | |
|---|---|
| (1) Cetostearyl alcohol | 3.5 |
| (2) Squalane | 40.0 |
| (3) Bee wax | 3.0 |
| (4) Reduced lanolin | 5.0 |
| (5) Ethyl para-hydroxybenzoate | 0.3 |
| (6) Polyoxyethene (20) sorbitan mono palmitate | 2.0 |
| (7) Monoglyceride stearate | 2.0 |
| (8) Sodium N-stearoyl glutamate | 0.5 |
| (9) 2-hydroxy-4-methoxy-benzophenone | 0.5 |
| (10) Octyl methoxycinnamate | 1.0 |
| (11) Retinol acetate | 2.0 |
| (12) Evening primrose oil | 0.05 |
| (13) Perfume | 0.03 |
| (14) EPC-Na | 0.1 |
| (15) 1,3-butylene glycol | 5.0 |
| (16) Polyethylene glycol 1500 | 5.0 |
| (17) Purified water | balance |

<Process>

Cetosteatyl alcohol, squalane, bee wax, reduced lanolin, ethyl para-hydroxybenzoate, polyoxyethylene (20) sorbitan monopalmitate, monoglyceride stearate, sodium N-stearoyl glutamate, 2-hydroxy-4-methoxy-benzophenone, octyl methoxycinnamate, retinol acetate and evening primrose oil were dissolved under heating (oil parts). Separately from this, EPC-Na, 1,3-butylene glycol and polyethylene glycol 1500 were dissolved in purified water and heated to 75° C. (water parts). Oil parts were added to water parts under stirring. After pulverizing the emulsified particles by a homomixer, the mixture was rapidly cooled under stirring to produce cream <Result>

| Sample | Suppressing Ratio |
|---|---|
| Example 2 | 82 |
| Without UV absorbent (components (9), (10)) | 38 |
| Without EPC—Na (component (14)) | 36 |
| Without UV absorbents and EPC—Na (components (9), (10) and (14)) | 36 |

EXAMPLE 3

Milky lotion

| | |
|---|---|
| (1) EPC—Mg | 0.2 |
| (2) 2-ethylhexyl para-dimethylaminobenzoate | 0.1 |
| (3) Mono-2-ethylhexyl diparamethoxycinnamate | 0.2 |
| (4) Stearic acid | 1.5 |
| (5) Cetyl alcohol | 0.5 |
| (6) Bee wax | 2.0 |
| (7) Polyoxyethylene (10) monooleate | 2.0 |
| (8) L-arginine | 0.3 |
| (9) Na L-glutamate | 0.02 |
| (10) PCA—Na | 0.05 |
| (11) Na hyaluronate | 0.01 |
| (12) Propylene glycol | 5.0 |
| (13) Glycerin | 3.0 |
| (14) Ethanol | 3.0 |
| (15) Ethyl para-hydroxybenzoate | 0.3 |
| (16) Perfume | 0.03 |
| (17) Carboxyvinyl polymer | 0.12 |
| (18) Purified water | balance |

<Process>

Perfume was dissolved in ethanol (alcohol parts). EPC-Mg, L-arginine, Na L-glutamate, PCA-Na, Na hyaluronate, propylene glycol, glycerin and carboxyvinyl polymer were dissolved in purified water under heating and the mixture was held at 70° C. (water parts). The other ingredients were mixed and dissolved under heating, and the mixture was held at 70° C. (oil parts). The oil parts were added to the water parts for preliminary emulsification and the mixture was uniformly emulsified by a homomixer. The alcohol parts were added to the emulsion under stirring. The mixture was cooled to 30° C. under stirring to obtain milky lotion.

<Result>

| Sample | Suppressing Ratio |
|---|---|
| Example 3 | 82 |
| Without UV absorbents (components (2), (3)) | 45 |
| Without EPC—Mg (component (1)) | 42 |
| Without UV absorbents and EPC—Mg (components (1), (2) and (3)) | 40 |

EXAMPLE 4

Foam mask

| | |
|---|---|
| (1) EPC—K | 0.02 |
| (2) 4-tert-butyl-4'-methoxy-dibenzoylmethane | 0.5 |
| (3) Stearic acid | 1.0 |
| (4) Behenylic acid | 1.0 |
| (5) Self-emulsification type glycerin monostearate | 1.5 |
| (6) Polyoxyethylene monostearate | 2.5 |
| (7) Batyl alcohol | 1.5 |
| (8) Perfume | 0.05 |
| (9) Glycerin | 5.0 |
| (10) 1,3-butylene glycol | 5.0 |
| (11) Polyethylene glycol 1500 | 3.0 |

-continued

| | |
|---|---|
| (12) Methyl para-hydroxybenzoate | 0.1 |
| (13) Potassium hydroxide | 0.15 |
| (14) Purified water | balance |
| (15) Liquified petroleum gas | 6.0 |
| (16) Dimethyl ether | 2.0 |

<Process>

EPC-K, glycerin, 1,3-butylene glycol, polyethylene glycol 1500, methyl para-hydroxybenzoate and potassium hydroxide were added to purified water and dissolved under heating at 70° C. The other ingredients except under heating, added to the mixture and were uniformly mixed. The resultant mixture was charged in a container. Finally, liquefied petroleum gas and dimethyl ether were added to the mixture as a spraying agent, thereby producing a foam mask.
<Result>

| Sample | Suppressing Ratio |
|---|---|
| Example 4 | 77 |
| Without UV absorbent (components (2)) | 41 |
| Without EPC—K (component (1)) | 43 |
| Without UV absorbent and EPC—K (components (1) and (2)) | 39 |

EXAMPLE 5
Ointment

| | |
|---|---|
| (1) EPC—Ca | 0.1 |
| (2) Octyl paradimethyl aminobenzoate | 4.0 |
| (3) Butylmethoxybenzoylmethane | 4.0 |
| (4) Tocopherol acetate | 0.5 |
| (5) Retinol palmitate | 1.0 |
| (6) Stearyl alcohol | 18.0 |
| (7) Japan wax | 20.0 |
| (8) Polyoxyethylene (10) monooleate | 0.25 |
| (9) Glycerin monostearate | 0.3 |
| (10) Vaseline | 32.0 |
| (11) Purified water | balance |

<Process>

EPC-Ca was added to purified water and the mixture was held at 70° C. (water parts). The other ingredients were mixed and dissolved at 70° C. (oil parts). The oil parts were added to the water parts and the mixture was uniformly emulsified by a homomixer. The mixture was then cooled to obtain ointment.

As described above, according to the external preparation of the present invention, since DL-α-tocopherol 2-L-ascorbic phosphoric diester and/or a salt thereof and at least one ultraviolet absorbing agent are contained, it is possible to suppress the cross-linking of collagen and to produce an excellent cutaneous aging resisting effect.

What is claimed is:

1. A method of treating a patient to resist cutaneous aging of the skin caused by cross-linking of collagen in the skin due to ultraviolet radiation, comprising applying to the skin an external preparation comprising: at least 0.005 wt % of DL-α-tocopherol 2-L-ascorbic phosphoric diester and/or a salt thereof; and at least 0.01 wt % of at least one ultraviolet absorbing agent, whereby cross-linking of collagen in the skin is suppressed when irradiated with ultraviolet rays, the wt % is based on the weight of the entire composition.

2. The method of claim 1, wherein the amount of said DL-α-tocopherol 2-L-ascorbic phosphoric diester and/or a salt thereof is 0.005 to 0.2 wt %.

3. The method of claim 1, wherein the amount of said ultraviolet absorbing agent is 0.01 to 15.0 wt %.

4. The method of claim 2, wherein the amount of said ultraviolet absorbing agent is 0.01 to 15.0 wt %.

5. The method of claim 1, wherein the ultraviolet absorbing agent is at least one of benzophenone ultraviolet absorbing agent.

6. The method of claim 3, wherein the ultraviolet absorbing agent is at least one of benzophenone ultraviolet absorbing agent.

7. The method of claim 4, wherein the ultraviolet absorbing agent is at least one of benzophenone ultraviolet absorbing agent.

8. The method of claim 1, wherein the ultraviolet absorbing agent is 2-hydroxy-4-methoxybenzophenone or its salt.

9. The method of claim 2, wherein the ultraviolet absorbing agent is 2-hydroxy-4-methoxybenzophenone or its salt.

10. The method of claim 3, wherein the ultraviolet absorbing agent is 2-hydroxy-4-methoxybenzophenone or its salt.

11. The method of claim 4, wherein the ultraviolet absorbing agent is 2-hydroxy-4-methoxybenzophenone or its salt.

* * * * *